(12) United States Patent
Geiger et al.

(10) Patent No.: US 7,536,216 B2
(45) Date of Patent: May 19, 2009

(54) METHOD AND SYSTEM FOR VIRTUAL ENDOSCOPY WITH GUIDANCE FOR BIOPSY

(75) Inventors: Bernhard Geiger, Cranbury, NJ (US); Guido M. Weiner, Berlin (DE)

(73) Assignees: Siemens Medical Solutions USA, Inc., Malvern, PA (US); Charite-Universitatsmedzin Berlin, Berlin (DE)

( * ) Notice: Subject to any disclaimer, the term of this patent is extended or adjusted under 35 U.S.C. 154(b) by 808 days.

(21) Appl. No.: 11/249,003

(22) Filed: Oct. 12, 2005

(65) Prior Publication Data
US 2006/0084860 A1    Apr. 20, 2006

Related U.S. Application Data

(60) Provisional application No. 60/619,809, filed on Oct. 18, 2004.

(51) Int. Cl.
*A61B 5/05*    (2006.01)
(52) U.S. Cl. .................. 600/407; 382/128; 345/45
(58) Field of Classification Search .............. 600/407, 600/410, 416, 420, 425, 431; 128/822, 920; 382/128; 348/45
See application file for complete search history.

(56) References Cited

FOREIGN PATENT DOCUMENTS

JP    2005 131319 A    5/2005
WO    WO 03/081351 A    10/2003
WO    WO 2005/043467 A    5/2005

OTHER PUBLICATIONS

Hopper K D et al: "Transbronchial biopsy with virtual CT bronchoscopy and nodal highlighting" Radiology Radiol. Soc. North America USA, vol. 221, No. 2, Nov. 2001, pp. 531-536, XP002372847 ISSN: 0033-8419 cited in the application the whole document.
Bricault I et al: "Registration of real and CT-derived virtual bronchoscopic images to assist transbronchial biopsy" IEEE Transactions on Medical Imaging IEEE USA vol. 17, No. 5, Oct. 1998, pp. 703-714, XP000922730 ISSN: 0278-0062 pp. 703-706.
Kiraly A P et al: planning for virtual Three-dimensional path bronchoscopy IEEE Transactions on Medical Imaging IEEE USA vol. 23, No. 11, Nov. 2004, pp. 1365-1379, XP002372848 ISSN: 0278-0062 the whole document.
Patent Abstracts of Japan vol. 2003, No. 12, Dec. 5, 2003.
A Vilianova I Bartoli: "Visualization Techniques for Virtual Endoscopy" Diss., TU Vienna, Sep. 2001, Extract: pp. i-v, 1-58, I-XI, eHB.
M. Kukuk: "A Model-Based Approach to Intraoperative Guidance of Flexible Endoscopy", Diss., Princeton, 2002, Extract: pp. i-xiv, 1-91; eHB.

*Primary Examiner*—Long V Le
*Assistant Examiner*—Saurel J Selkin
(74) *Attorney, Agent, or Firm*—Donald B. Paschburg (57) ABSTRACT

A method for virtual endoscopy in a lumen includes acquiring from a patient an imaging dataset exhibiting a lesion external to a lumen wall; deriving a three-dimensional (3-D) volume of the lesion; obtaining data on maximum bend characteristics for a given endoscope; and deriving projection criteria, based on the 3-D volume and the maximum bend, for projecting an endoluminal image of said lesion, indicating an optimal biopsy insertion point.

55 Claims, 7 Drawing Sheets

METHOD AND SYSTEM FOR VIRTUAL ENDOSCOPY WITH GUIDANCE FOR BIOPSY

CROSS-REFERENCE TO RELATED APPLICATIONS PRIORITY

Specific reference is hereby made to U.S. Provisional Application No. 60/619,809, entitled VIRTUAL ENDOSCOPY WITH VISIBLE EXTRA-LUMINAL STRUCTURES FOR BIOPSY GUIDANCE, filed Oct. 18, 2004 in the name of Bernhard Geiger and Guido Weiner, the inventors in the present application, and of which the benefit of priority is claimed and whereof the disclosure is hereby incorporated herein by reference.

The present application relates generally to the field of virtual endoscopy and, more particularly, to virtual endoscopy with guidance for biopsy procedures.

BACKGROUND OF THE INVENTION

Trans-Bronchial Needle Aspiration (TBNA) is a procedure utilizing a biopsy needle for obtaining tissue samples from the lung regions of a medical patient for purposes of examination and related procedures. During TBNA, the orientation of the insertion and the selection of a biopsy site for the needle are generally determined by a bronchoscopist, and typically, this is based on images obtained by computerized tomography (CT). As such, TBNA is a routinely used and relatively safe intervention for the diagnosis and staging of hilar lesions, these being lesions relating to lymph nodes of the lung. These are generally in the form of nodules. The specificity of the procedure is close to 100%, meaning that nearly all nodules identified as such by the procedure are in fact such nodules. See the paper by Win, T., et al. entitled "The role of transbronchial needle aspiration in the diagnosis of bronchogenic carcinoma," Resp Care, June 2003; 48(6): 602-605.

The sensitivity of the procedure is variously reported to be between 47% and 73%, meaning the percentage of nodules found and identified as such by the procedure out of the set of actually existing nodules. See the publications by: Patelli, M., et al. entitled "Role of fiberoscopic transbronchial needle aspiration in the staging of N2 disease due to non-small cell lung cancer," Ann Thoracic Surg, 2002; 73: 407-411; Xie, H. B. et al., entitled "Bronchoscopy Guided Transtracheal and Transbronchial Fine Needle Aspiration Biopsy: A 5-year institutional review of 111 cases," Diagn. Cytopathol. 2002; 27(5): 276-281; and Harrow, E. M. et al., entitled "The utility of transbronchial needle aspiration in the staging of bronchogenic carcinoma," Am J Respiratory Crit Care Med 2000; 161: 601-607.

The reasons for false negatives include insufficient tissue samples, non-relevant tissue samples, and biopsies made at wrong locations. Generally, the biopsy is carried out from within the airway wall in an outward direction and typically, the lymph nodes cannot be seen from inside the airway tube.

In a pilot study, McAdams et al. used virtual bronchoscopy to improve the orientation of TBNA by displaying the target volumes. The study was performed using single slice spiral CT. The patients underwent a CT thorax acquisition with 10 mm slice thickness. Additional 3-5 mm slices were obtained from patients with mediastinal or hilar lesions, which were then used for virtual bronchoscopy. The mediastinum is the space in the chest between the pleural sacs of the lungs that contains all the viscera of the chest except the lungs and pleurae.

Snapshots of relevant positions were taken and displayed together with the axial CT images during the bronchoscopy. The time required for calculating virtual endoscopy was 20-35 min, marking of the targets took 5 min and creating the film took another 30-60 min. The authors report a sensitivity of 88%, but did not compare the results to the traditional procedure. See the publication by McAdams, H. P. et al. entitled "Virtual bronchoscopy for directing transbronchial needle aspiration of hilar and mediastinal lymph nodes: a pilot study," AJR 1998; 170: 1361-1364.

In another study, Hopper et al. create virtual endoscopy with marked target volumes from 3 mm CT images. TBNA was only executed virtually, based on axial CT only or virual bronchoscopy with overlayed target volumes. The authors describe a higher rate of success; however, the study is not based on clinical data. See the publication by Hopper, K. D. et al, entitled "Transbronchial biopsy with virtual CT bronchoscopy and nodal highlighting," Radiology, 2001; 221: 531-536.

However, for conducting an investigation of an area of interest, typically the end portion of the endoscope needs to be bent through approximately a right angle so that the tip of the endoscope faces the area of interest, generally the lesion being examined. This is achieved by pushing in the endoscope so as to jam it against the side of the wall opposite the area of interest until the required orientation is achieved.

In a typical prior art procedure, the endoscope is pushed in, up to a reference point, such as down against the carina and the insertion reference depth of the actual endoscope is read off a scale on the endoscope. The endoscope is then withdrawn until the scale shows that the end of the endoscope should now be at the point where the lymph node is estimated to be, based on imaging. However, the actual withdrawal has to be somewhat less to make allowance for the length required for the right angle bend to enable the endoscope end to face the side wall. The endoscope is then pushed in so as to angle it against the wall and point it to where the lymph node is supposed to be. Some guesswork and estimation is required, particularly in view of the angle through which the end portion of the endoscope needs to be bent. Errors may occur in these estimations, causing the biopsy to miss the desired target.

BRIEF SUMMARY OF THE INVENTION

It is herein recognized that, while the foregoing results tend to indicate that virtual bronchoscopy can improve TBNA, yet nevertheless, the methods presented are too time consuming for clinical routine use.

It is furthermore herein recognized that the CT data contains more information beyond that which is exploited in the prior art methods.

In accordance with principles of the present invention, the information contained in the CT data can be utilized to improve the selection of the biopsy sites in order to improve the yield and the sensitivity.

In accordance with an aspect of the present invention, the invention enables the routine use of virtual bronchoscopy in a clinical workflow to increase the yield of TBNA, including tools to exploit relevant information contained in the CT data.

In accordance with another aspect of the invention, a method for virtual endoscopy in a lumen includes acquiring from a patient an imaging dataset exhibiting a lesion external to a lumen wall; deriving a three-dimensional (3-D) volume of the lesion; obtaining data on maximum bend characteristics for a given endoscope; and deriving projection criteria, based on the 3-D volume and the maximum bend, for projecting an endoluminal image of said lesion, for indicating an optimal biopsy insertion point.

In accordance with an aspect of the invention, a method for virtual endoscopy in a lumen comprises: acquiring from a patient an imaging dataset including a lesion external to a lumen wall; generating multiplanar reformations (MPRs) from the dataset; drawing planar contours around the lesions in the MPRs; deriving a three-dimensional (3-D) volume of the lesion from the contours; determining distances from a reference point to the start and end of the lesion; determining the distance from the reference point to a virtual endoscope in the lumen; obtaining data on maximum bend characteristics for a endoscope in a lumen of a given diameter; deriving projection criteria, based on the 3-D volume, the lumen diameter, and the maximum bend characteristics; projecting an endoluminal image of the lesion based on the projection criteria, the endoluminal image indicating an optimal biopsy insertion point; and deriving corrected values for the foregoing distances allowing for the maximum bend characteristics.

In accordance with another aspect of the invention, the step of deriving projection criteria comprises deriving a set of surface normals to the lumen wall and changing the respective angles of the normals based on the 3-D volume, the lumen diameter, and the maximum bend characteristics for obtaining a set of modified normals.

In accordance with another aspect of the invention, the step of projecting an endoluminal image of the lesion comprises utilizing the set of modified normals to define the endoluminal image.

In accordance with another aspect of the invention, the step of projecting an endoluminal image comprises a step of indicating thereon the respective depths of the lesion corresponding to respective points on the endoluminal image.

In accordance with another aspect of the invention, the step of indicating respective depths comprises a step of determining the respective depths along respective ones of the set of modified normals.

In accordance with another aspect of the invention, the step of projecting an endoluminal image comprises a step of indicating thereon the respective depths of the lesion corresponding to respective points on the endoluminal image.

In accordance with another aspect of the invention, the step of indicating the respective depths of the lesion comprises one of either (a) shading the image to indicate depth or (b) color coding the image to indicate depth.

In accordance with another aspect of the invention, the method includes a step of outputting information on the rotational angle of the virtual endoscope.

In accordance with another aspect of the invention, the method includes a step of performing a real endoscopy utilizing information from the virtual endoscopy, including identifying the reference point, utilizing the corrected values, and the respective depths for inserting a biopsy needle at the optimal biopsy insertion point.

In accordance with another aspect of the invention, the method includes a step aligning the biopsy needle along a respective modified normal at the optimal biopsy insertion point.

In accordance with another aspect of the invention, the method includes a step of performing a real endoscopy utilizing information from the virtual endoscopy, including identifying the reference point, utilizing the corrected values, the information on the rotational angle, and the respective depths for inserting a biopsy needle at the optimal biopsy insertion point.

In accordance with another aspect of the invention, wherein the step of acquiring from a patient an imaging dataset comprises acquiring a data set of the bronchial airway.

In accordance with another aspect of the invention, a method for virtual endoscopy in a lumen comprises: acquiring from a patient an imaging dataset exhibiting a lesion external to a lumen wall; forming an image from the dataset; drawing planar contours around the lesion; deriving a three-dimensional (3-D) volume of the lesion; obtaining data on maximum bend characteristics for a given endoscope; and deriving projection criteria, based on the 3-D volume and the maximum bend, for projecting an endoluminal image of the lesion, indicating an optimal biopsy insertion point.

In accordance with another aspect of the invention, a system for virtual endoscopy in a lumen, comprises: apparatus for acquiring from a patient an imaging dataset exhibiting a lesion external to a lumen wall; generating multiplanar reformations (MPRs) from the dataset; drawing planar contours around the lesion; apparatus for deriving a three-dimensional (3-D) volume of the lesion; apparatus for obtaining data on maximum bend characteristics for a given endoscope; and apparatus for deriving projection criteria, based on the 3-D volume and the maximum bend, for projecting an endoluminal image of the lesion, indicating an optimal biopsy insertion point.

In accordance with another aspect of the invention, a method for virtual endoscopy in a lumen, comprises: acquiring a dataset from a patient using an imaging technique such as CT or MRI; generating multiplanar reformations (MPRs) from the dataset, comprising two-dimensional (2D) sections; displaying a virtual endoscopic view utilizing the dataset; drawing planar contours around lesions in the MPRs; calculating a 3-D volume from the planar contours; displaying the 3-D volume in an endoluminal view; selecting a reference point; utilizing software to display the distances between the reference point to the start and endpoints of a lesion and to a virtual endoscope position; utilizing software to display the maximal bending angle of an endoscope in a selected insertion area, a corrected distance to the reference point after bending, and to project an insertion point onto the endoluminal wall in the selected insertion area, and optionally, to display rotational information; and guiding a real endoscope in a patient to the insertion point using information from the virtual bronchoscopy.

In accordance with another aspect of the invention, a computer program product comprises a computer useable medium having computer program logic recorded thereon for program code for performing a method for virtual endoscopy in a lumen, comprising: acquiring from a patient an imaging dataset exhibiting a lesion external to a lumen wall; deriving a three-dimensional (3-D) volume of the lesion; obtaining data on maximum bend characteristics for a given endoscope; and deriving projection criteria, based on the 3-D volume and the maximum bend, for projecting an endoluminal image of the lesion, indicating an optimal biopsy insertion point.

In accordance with another aspect of the invention, a method for virtual endoscopy within a cavity comprises: acquiring from the cavity an imaging dataset including a feature of interest external to a cavity wall; drawing contours around the feature; deriving a three-dimensional (3-D) volume of the feature from the contours; determining distances from a reference point to the start and end of the feature; determining the distance from the reference point to a virtual endoscope in the cavity; obtaining data on maximum bend characteristics for the endoscope corresponding to the cavity dimensions; deriving projection criteria, based on the 3-D volume, the cavity dimensions, and the maximum bend characteristics; projecting an endoluminal image of the feature based on the projection criteria, the endoluminal image indicating an optimal access point; and deriving corrected values for the foregoing distances allowing for the maximum bend characteristics.

In accordance with another aspect of the invention, a method for virtual endoscopy in a cavity, comprises: acquiring an imaging dataset exhibiting a feature of interest external to a wall of the cavity; deriving a three-dimensional (3-D) volume of the feature of interest; obtaining data on maximum bend characteristics for a given endoscope; and deriving projection criteria, based on the 3-D volume and the maximum bend, for projecting an endoluminal image of the feature of interest.

BRIEF DESCRIPTION OF THE DRAWINGS

The invention will be more fully understood from the detailed description which follows, in conjunction with the drawings, in which.

DETAILED DESCRIPTION OF THE INVENTION

In the description following, reference is made to DICOM images: DICOM refers to "Digital Imaging and Communications in Medicine," which is a protocol used for medical images and which generally facilitates compatibility between different medical imaging devices.

Data is acquired from an imaging system such as CT or MRI. The system reads DICOM images and displays "transparent" virtual bronchoscopy images showing structures behind the lumen wall. Virtual bronchoscopy is possible in real time and can be used at the same time as the actual bronchoscopy. Segmentation of the lymph nodes may be carried out based on injected contrast material or without contrast material in the case of lymph nodes which are visible on a non-contrast CT set. In accordance with an embodiment of the present invention, two displays are before the bronchoscopist, essentially side by side: a virtual display derived from imaging information from the patient and a real or actual endoscopic view obtained from an endoscope inserted into the patient.

Multiplanar reformations (MPR), comprising two-dimensional (2D) sections are generated and the software shows axial, coronal, and sagittal displays of the data. For a description of multiplanar reformation see, for example, Rogalla et al., "Virtual Endoscopy and Related 3D Techniques," Springer-Verlag, 2001, 2002; pp. 50 et seq. Coronal refers to the frontal plane that passes through the long axis of the body and sagittal refers to the median plane of the body or any plane parallel to it.

In accordance with the invention, objects drawn on the MPR images, for example by hand, can be seen in the virtual endoscopic display, with different shading according to the distance from the lumen wall. Furthermore, the simulated optical properties of the virtual endoscope, e.g. the viewing angle of the virtual camera on the end of the endoscope, can be adjusted to match the viewing angle of the real endoscope so that the real and virtual endoscopy views correspond. The posterior wall of the lumen is displayed at the bottom of the image, which facilitates correct orientation. Distances and angles can be measured, in addition to purely visual information. The endoscopist can specify anatomical landmarks, such as the carina or other feature, as reference points, from which the distance to the needle insertion point is calculated. The endoscopist draws contours corresponding to the lesion image on the MPR image. Alternatively, the endoscopist can start with drawing the lesions and set reference points later.

A three-dimensional (3D) volume is then calculated from the planar contours. The maximum bending angle and associated shortening or foreshortening of the endoscope length is calculated in the virtual endoscopy. Wall normals in the vicinity of the lesion are modified by deflecting their angles in accordance with information on the bending properties of the bronchoscope and the lumen diameter at the level of interest to intersect with the lesion mass and enable projection of the insertion point onto the endoluminal wall as a target point for the biopsy needle. This is equivalent to modifying the projection angle of the lesion onto the lumen wall, as described later. Based on a feature identifiable in both the virtual and real bronchoscopies, and on insertion depth information obtained from the virtual bronchoscopy, the corresponding target point in the real bronchoscopy is identified and utilized for orientation and insertion of the biopsy needle to the desired depth for biopsy. Aspiration of tissue through the needle then provides the biopsy sample.

In outline, a method in accordance with the invention comprises:

acquiring a dataset from a patient using an imaging technique such as CT or MRI;

displaying a virtual endoscopic view utilizing the dataset;

drawing planar contours around lesions in the MPRs;

calculating a 3-D volume from the planar contours;

displaying the 3-D volume in an endoluminal view;

selecting a reference point;

utilizing software to display the distances between the reference point to the start and endpoints of a lesion and to a virtual endoscope position;

utilizing software to display the maximal bending angle of the endoscope in a selected insertion area, the corrected distance to the reference point after bending, and to project an insertion point onto the endoluminal, and optionally, to display rotational information; and guiding the real endoscope in a patient to the insertion point using information from the virtual bronchoscopy.

Figure 1:
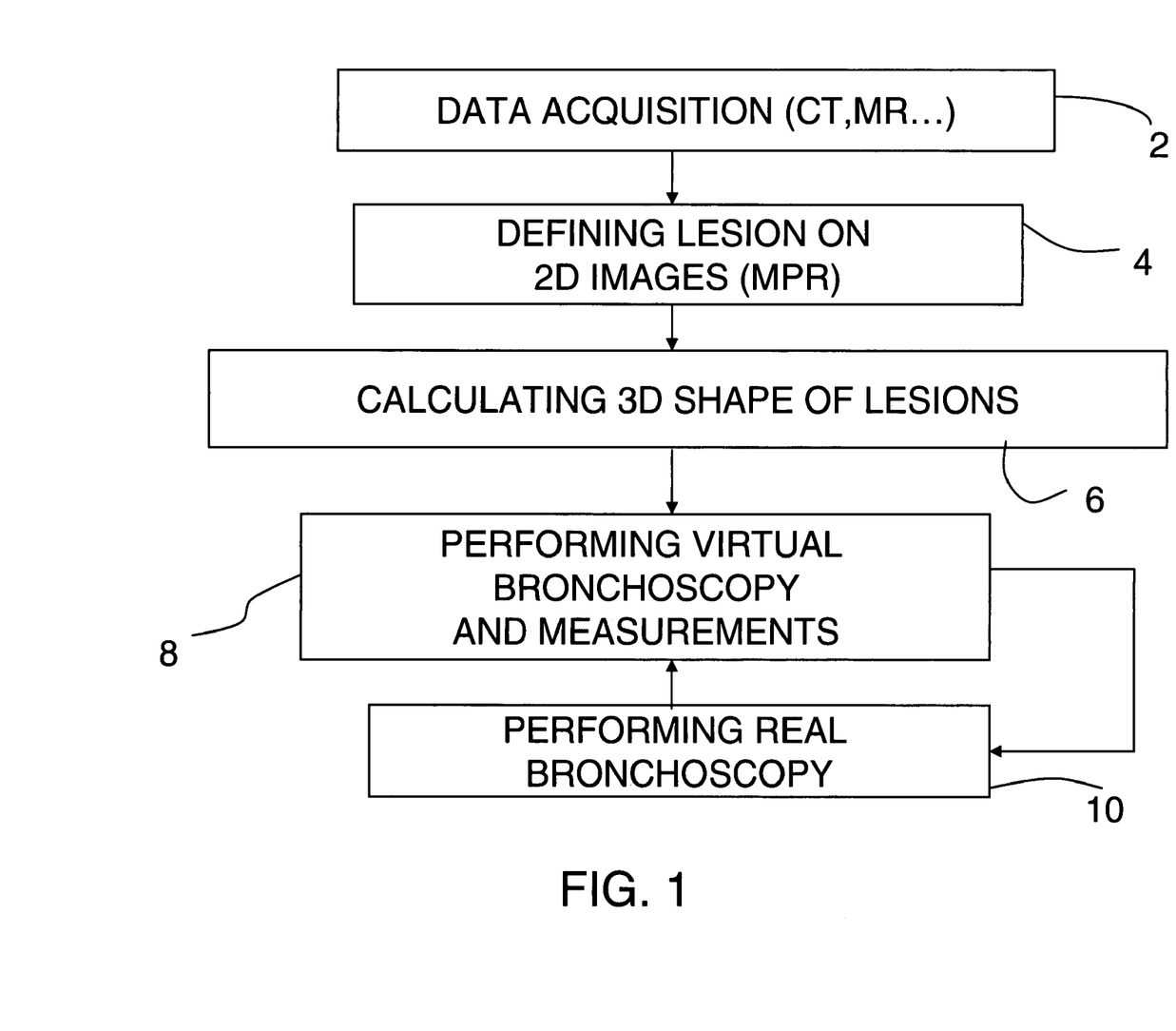
FIG. 1 shows a work flow diagram in accordance with principles of the present invention.

FIG. 1 shows an overview of steps of an exemplary embodiment in accordance with the method of the invention. Steps 2, 4, 6 and 8 relate to virtual steps performed on a dataset derived at an earlier point in time by imaging procedures. Step 10 relates to procedures involving the use of a real endoscope on a patient in person. In step 2, image data is acquired from a patient, utilizing, for example, computer-aided tomography (CT) or magnetic resonance (MR) imaging, or other technique. In step 4, recognized lesions are defined on 2-dimensional (2D) images formed as described above. Lesion recognition may be done by a radiologist and suitably entered as markings on the 2D images using known techniques. Contours are drawn around the lesions in the MPR from which a 3-D volume is calculated and displayed in the endoluminal view, with different shading or coloring in accordance with the distance from the wall. Generally, the lesion is drawn on top of the wall using blending, so that the wall appears to be transparent. Automated and semi-automatic techniques are also possible. In step 6, the 3-dimensional (3-D) shape of the lesions is derived, for example, by using a technique such as the "nuages" which uses Delaunay triangulation.

In step 8, a virtual bronchoscopy is performed, wherein a position and an orientation for the virtual endoscope are defined in the trachea, where the orientation corresponds to the center axis of the real endoscope. The initial position of the virtual endoscope can be selected on the MPR using the computer mouse or it can be calculated automatically in the trachea. Typically, these are defined in the topmost level of the trachea, followed by "flying through" or "flying down", in accordance with known techniques.

A perspective virtual view is then generated by utilizing a technique such as ray casting, for example. The virtual field of view, corresponding to the field of view of the real endoscope, can then be selected.

Figure 4:
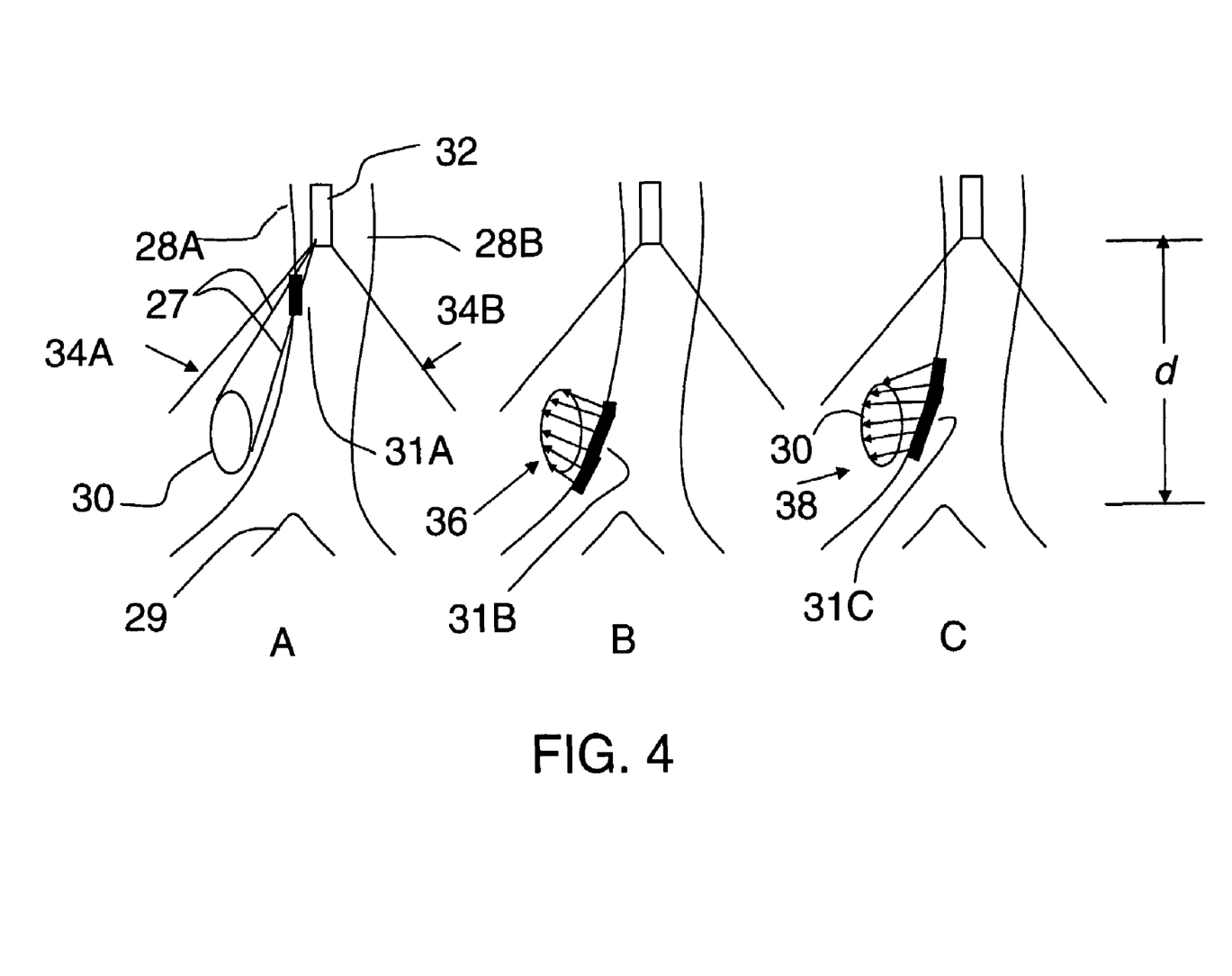
FIG. 4 includes a diagram, not necessarily to scale, of the drawing projection of a 3-D lesion in accordance with principles of the present invention.

A projection image of the 3D lesion is then "virtually projected" onto the virtual wall of the trachea or airway such that the wall is represented as being virtually transparent, as noted above, so that the lesion, which is outside the wall can be seen "through" the virtual wall. The projection can be in accordance with different methods. For example, FIG. 4A shows a perspective projection A of a lesion B onto the wall, simulating a perspective view from the endoscope position at C. This will be further described in conjunction with FIG. 4. Step 10 in FIG. 1 comprises performing a real bronchoscopy on an actual patient, in conjunction with a view of the images resulting from virtual bronchoscopy in step 8 and the associated measurements, as will hereinafter be described.

It is noted that the real bronchoscopy can be executed after the virtual, using information from the virtual, including measurements, screenshots, movies, and so forth, or it can be done in parallel, for comparing virtual and real views.

FIGS. 4A, 4B, and 4C respectively show a perspective projection, not necessarily to scale; an orthogonal projection onto an airway wall; and a projection onto an airway wall taking into account the maximal possible bending of the endoscope, in accordance with the principles of the present invention.

FIG. 4A shows a diagrammatic representation of a trachea 28A and 28B, with an endoscope 32 positioned therein. A carina 29 represents a ridge defining the place where trachea divides into two branches. The angle or field of view of endoscope 32 is indicated by the bounding lines 34A and 34B. A lesion in the field of view is represented by a mass 30. An indication 31A is generated on the inside surface of the wall of the trachea, for example by using a different surface coloration, at points where rays 27 from lesion 30 to endoscope 32 intercept the wall of the trachea in a perspective type of projection, so as to provide an indication of the lesion, having a relationship to the lesion outside the wall.

While such a technique can provide some information for inserting a biopsy needle, it is not optimal for the selection of an insertion point and direction for the biopsy needle. For example, image 31A is not close to lesion 3 and the two are related in a perspective projection manner such that the insertion of a biopsy needle from inside the trachea will, in general, not be readily or easily well guided into lesion 30.

FIG. 4B shows another technique utilizing orthogonal projection onto the airway wall. Surface normals are extended from the wall of the trachea. Some of the normals will intercept the lesion mass and, when this happens, an indication is provided, such as by changing the color of the area on the inside of the virtual wall from which the intercepting normals extend. In the example shown in FIG. 4B, the darkest color is used to indicate the thicker part of the lesion where needle insertion is preferred; the remainder of the lesion is shown by a second, lighter color.

While this technique is an improvement over the previously described perspective technique for providing guidance for the insertion of a biopsy needle, it does not take into account the view changes which result from the afore-mentioned bending of the endoscope tip, substantially with its axis normal or close to normal to the wall surface. Furthermore, as indicated in FIG. 4B, the biopsy mass will not necessarily be aligned with a major axis parallel to the airway wall, thereby reducing the chance of a biopsy needle inserted near the center of image 31B for hitting the thickest part of the lesion, as is typically desirable for obtaining a better biopsy sample.

FIG. 4C shows a method of projection in an embodiment in accordance with the principles of the present invention, wherein the image projected onto the wall is formed with an allowance for the bending of the endoscope. In effect, the original surface normals are tilted by an angle in accordance with the bending of the endoscope end, corresponding to the bending angle as known for the real endoscope It is noted that the resulting projected image is such that there is typically a greater chance for a biopsy needle inserted along the direction of the tilted surface normals in hitting a thicker part of the lesion, which is advantageous in obtaining a valid biopsy specimen.

In general conformity with the outline shown in FIG. 1, the method of the present invention is now described in greater detail. In reference to FIG. 2, in which all of the steps 12-18 relate to the virtual bronchoscopy, in accordance with step 12, the virtual bronchoscopy comprises defining a position and an orientation for the virtual endoscope in the trachea. The initial position of the virtual endoscope can be selected on the MPR using the computer mouse, or it can be calculated automatically in the trachea. The lesion is drawn on top of the wall using blending, so that the wall appears to be transparent.

Figure 2:
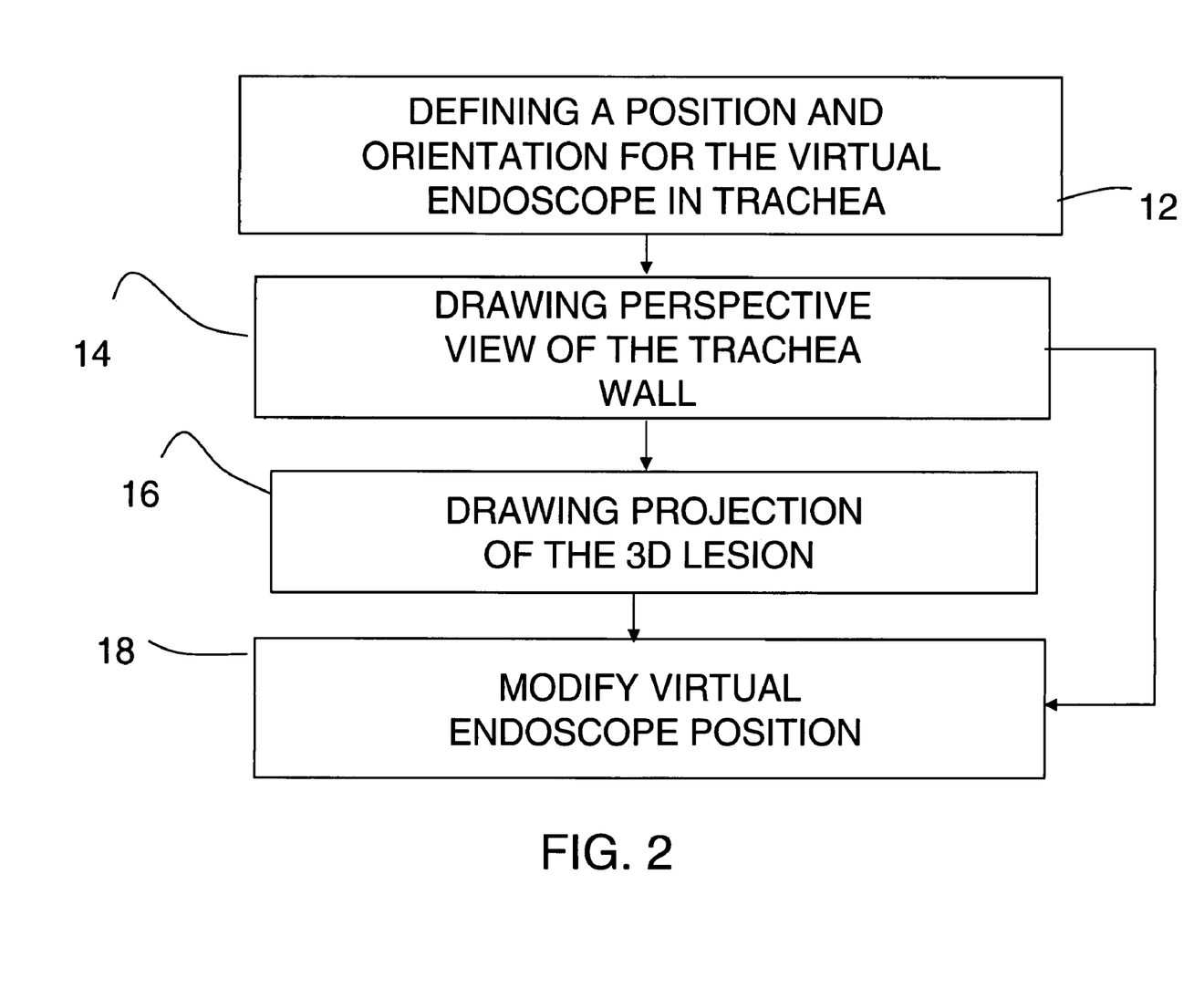
FIG. 2 shows a flow diagram for virtual bronchoscopy in accordance with principles of the present invention.

A perspective view of the trachea wall (Step 14) and a projection of the 3-D lesion are drawn, as in step 16. Depending upon the result achieved, the virtual endoscope position is then modified as may be necessary, as in step 18.

Figure 3:
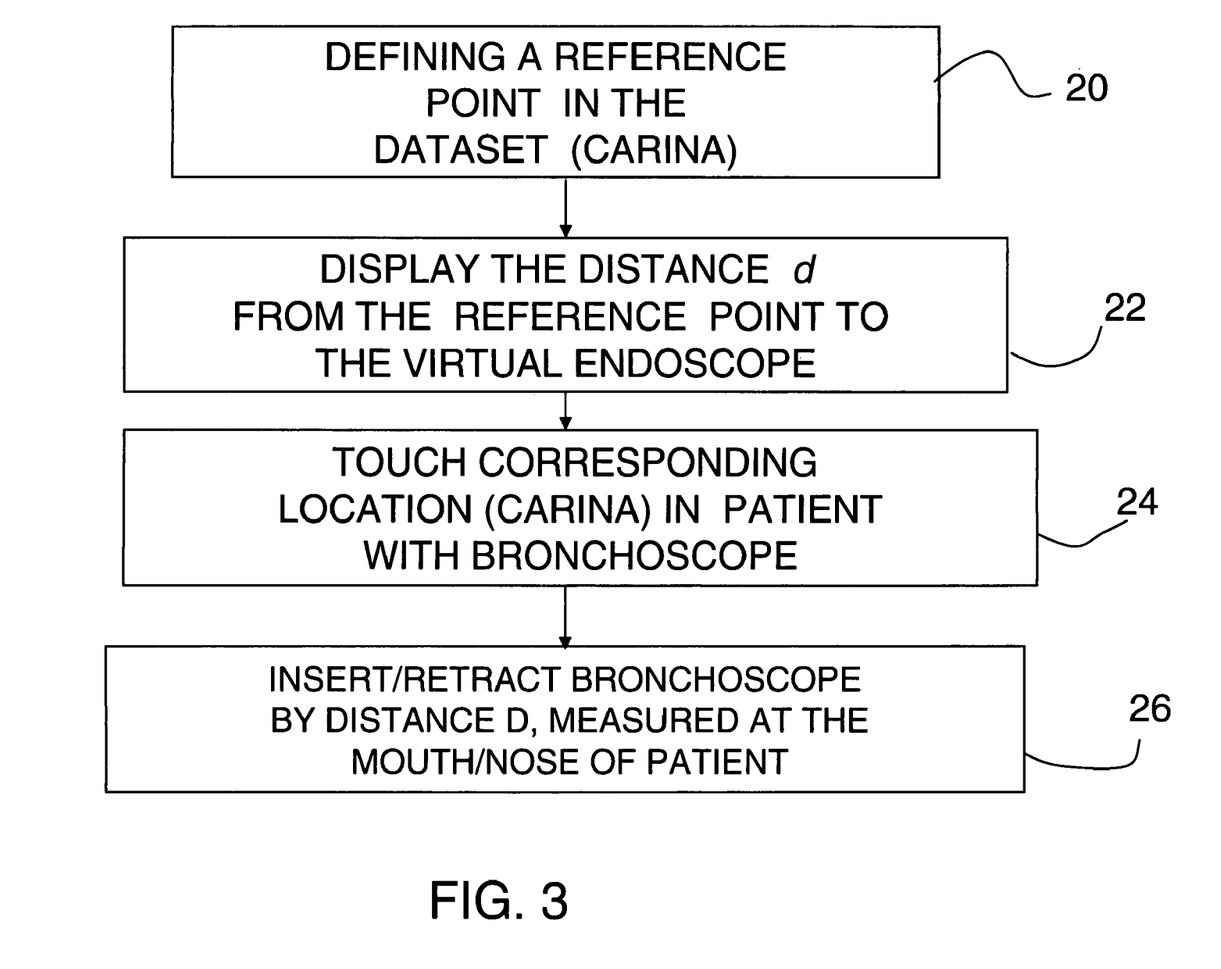
FIG. 3 shows a flow diagram for position measurements in virtual bronchoscopy in accordance with principles of the present invention.

In FIG. 3, steps 20 and 22 refer to the virtual bronchoscopy and steps 24 and 26 relate to the real endoscopy on a real patient. Referring to the virtual endoscopic procedure and to steps 20 and 22 in FIG. 3, a reference point in the dataset is defined which is identifiable in both the virtual and real endoscopic procedures. This is typically the carina or ridge at the point of bifurcation of the airway. The distance from this reference point to the virtual endoscope is then determined and displayed, referred to as "d" in FIG. 4C. The reference point is defined interactively on the MPR or in the virtual view by clicking with a computer mouse.

The real bronchoscopy on an actual patient may be undertaken concurrently with the virtual bronchoscopy or it may be performed serially therewith. In the real bronchoscopy, step 10 in FIG. 1, the bronchoscopist performing the procedure inserts the bronchoscope and touches the end of the (real) bronchoscope to the point in the (real) patient corresponding to the reference point in the virtual endoscopy, in this case the carina.

Typically, after insertion the bronchoscope is then retracted by the distance d, as measured at the mouth or nose of the patient, or nose. Typically such bronchoscopy is performed through the patient's nose.

Figure 5:
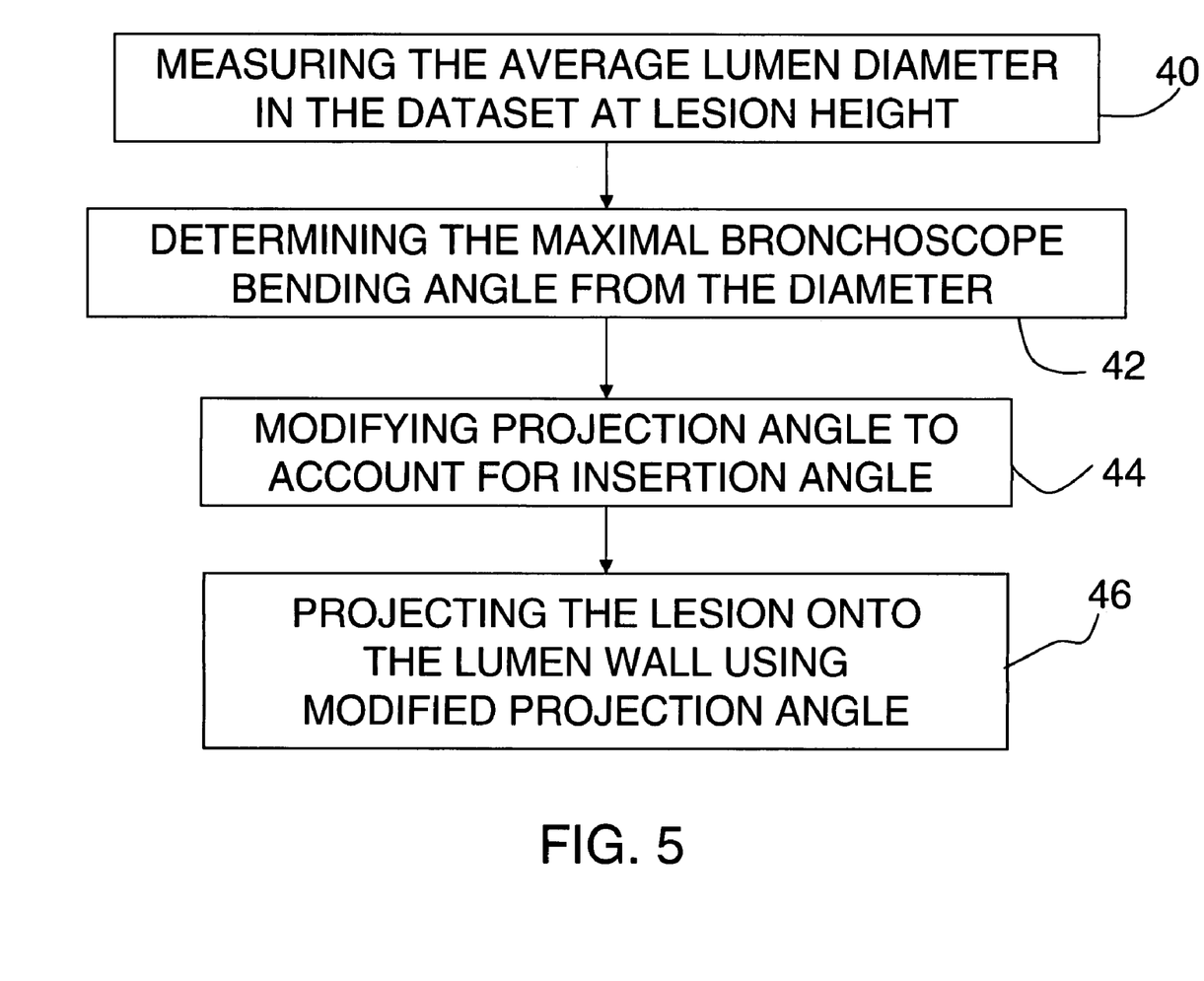
FIG. 5 shows a flow diagram for image projection onto an airway wall taking into account the maximal possible bending angle for a given endoscope.

In FIG. 5, all of the steps 40-46 relate to the virtual bronchoscopy dataset. Using data from the virtual bronchoscopy, the inside diameter of the lumen of the airway is determined from the virtual image dataset corresponding to the level or height of the lesion under consideration (Step 40 in FIG. 5). The angle through which the bronchoscope can be bent is dependent on this inside diameter. Using this information, together with information relating to the particular type of bronchoscope in use, the maximum bending angle of the bronchoscope is determined (Step 42 in FIG. 5). In FIG. 5, step 44, the image projection angle is then modified and set to correspond to take account of this bending angle by tilting the surface normals by a corresponding amount to achieve a modified projection angle as shown in FIG. 4C. If the maximum bending angle is $\alpha \leqq 90$ degrees, then this projection can be obtained by rotating the surface normals by $(90-\alpha)$ degrees around the normal of the plane defined by the surface normal and the endoscope axis. Then, using the modified projection angle, the lesion is projected onto the lumen wall, as shown in step 46 in FIG. 5.

Figure 6A:
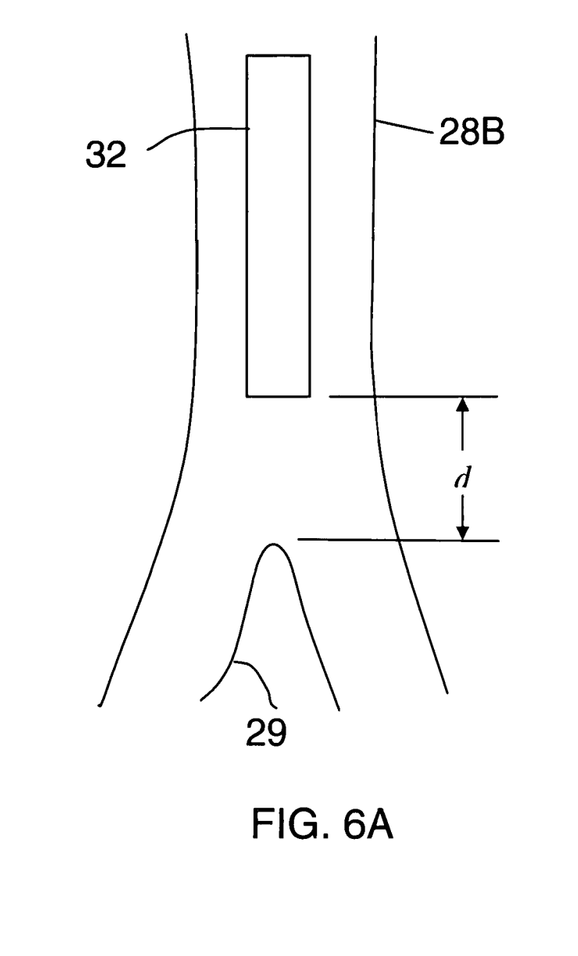
FIG. 6 shows diagrams, not necessarily to scale, indicating measurements to a reference point with and without endoscope bending, in accordance with principles of the present invention.
Figure 6B:
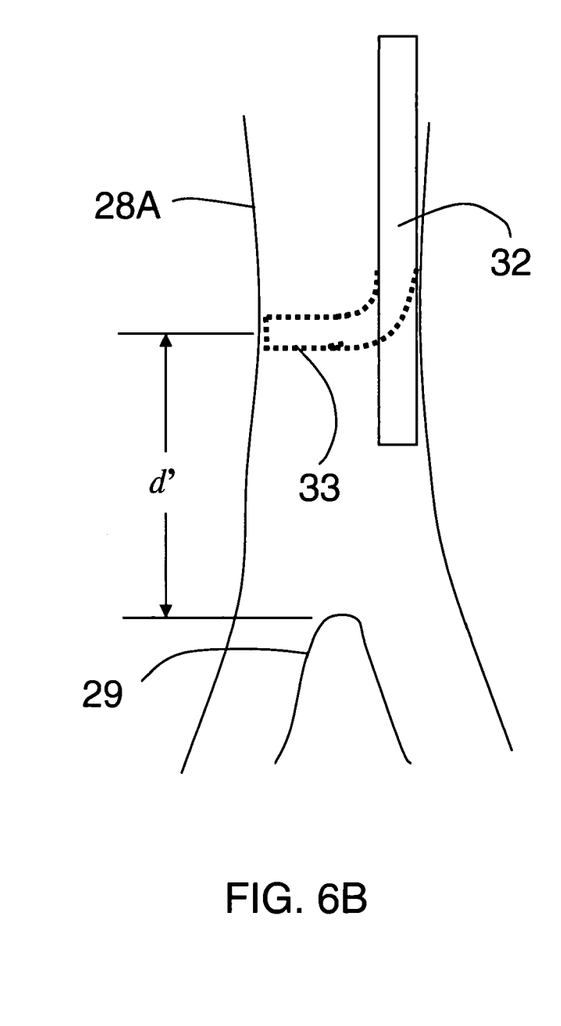

FIG. 6A shows the measurement d, as obtained from the virtual bronchoscopy dataset. It can also be compared optically. FIG. 6B shows the measurement d' which is the distance between the carina and the endoscope after it has been bent to face the area under consideration.

In the real bronchoscopic procedure, the biopsy needle is then inserted for obtaining a sample, based on the projected image in the virtual bronchoscopy as it appears from the inside of the transparent virtual wall.

For example, if the maximum bending angle is 90 degrees, the lesion is projected onto the surface using a projection angle of 90 degrees, i.e. orthogonally, and so forth for other angles. Thus, a biopsy needle inserted at the projected location of the lesion at this same angle will hit the lesion.

For each different endoscope model, the maximum bending angle can be determined from a table of related experimental results or it can be determined by using a model based method such as that described by Kukuk et al. See Markus Kukuk, B. Geiger, "*Registration of real and virtual endoscopy—a model and image based approach*", Medicine Meets Virtual Reality 2000, Newport Beach, CA, Jan. 20-24, 2000, IOS Press, pp. 168-174.

The present invention has been described by exemplary embodiments as applied to endoscopy in general and bronchoscopy in particular. The invention is also applicable to various alternative environments, human and non-human, in which suitable cavities having a certain degree of rigidity exist, such as for example a sinus cavity, such that a correspondence between pre-operative data and the subject patient can be found.

The present invention is also applicable, with suitable minor modifications as may be required, to industrial applications such as the inspection of tubular cavities, conduits, sewer pipes, and so forth, for which drawings or blueprints or other data are available.

Figure 7:
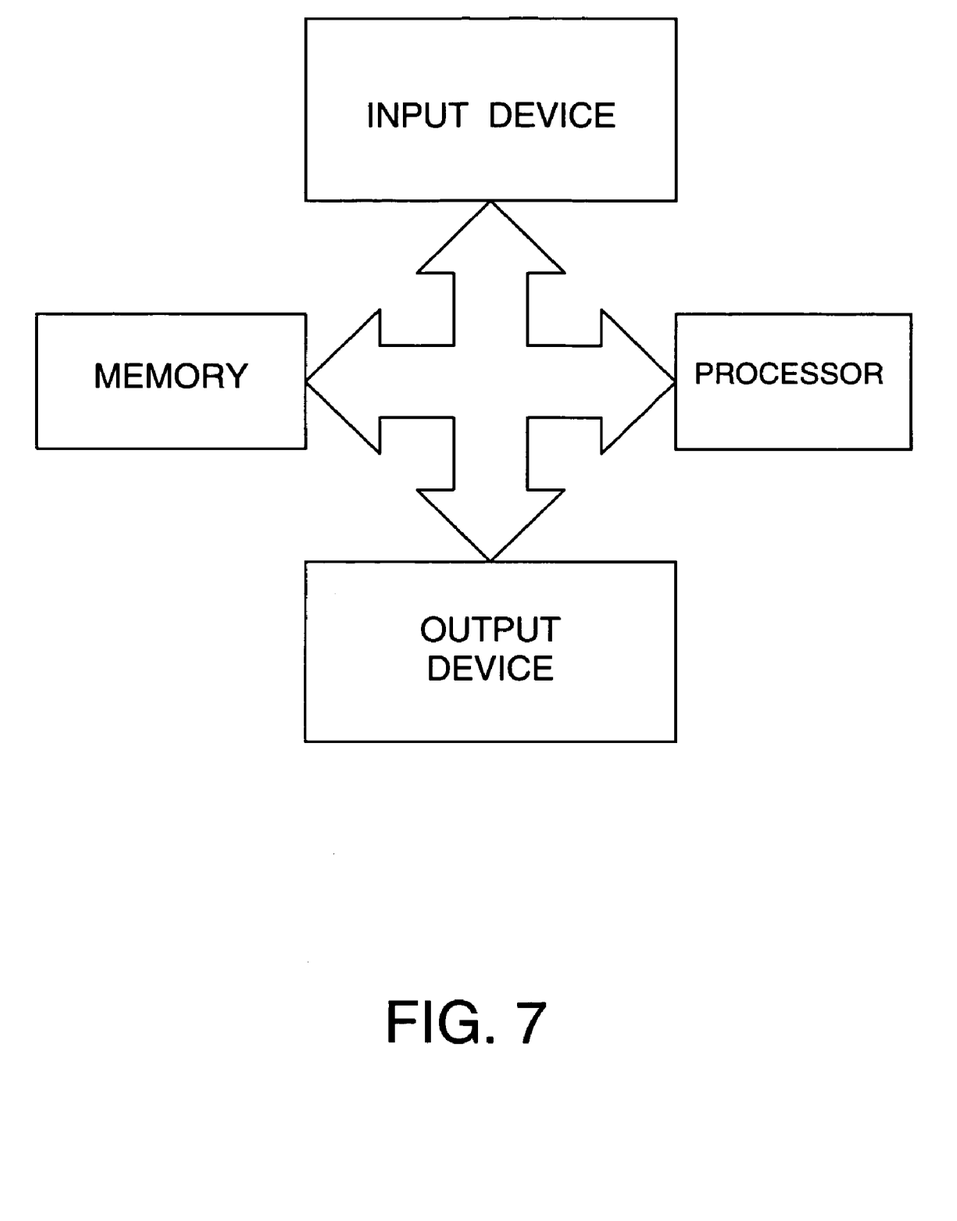
FIG. 7 shows a block schematic diagram showing the use of a computer in performing the method in accordance with principles of the present invention.

As will be apparent, the present invention is intended to be implemented with the use and application of a programmed digital computer. FIG. 7 shows in basic schematic form a digital processor coupled for two way data communication with an input device, an output device, and a memory device for storing a program and other data. The input device is so designated in broad terms as a device for providing an appropriate image or images for processing in accordance with the present invention. For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may include a computer type display device using any suitable apparatus such as a cathode-ray kinescope tube, a plasma display, liquid crystal display, and so forth, or it may or may not include a device for rendering an image and may include a memory device for storing an image for further processing, or for viewing, or evaluation, as may be convenient, or it may utilize a connection or coupling including such as are noted above in relation to the input device. The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing image processing utilizing the method of the present invention.

While the present invention has been described by way of exemplary embodiments, it will be understood by one of skill in the art to which it pertains that various substitutions, changes, and modifications in matters of detail which, while not herein explicitly described, may be made without departing from the spirit of the invention, which is defined in the claims following.

What is claimed is:

1. A method for virtual endoscopy in a lumen, comprising:
   acquiring from a patient an imaging dataset including a lesion external to a lumen wall;
   generating multiplanar reformations (MPRs) from said dataset;
   drawing planar contours around said lesions in said MPRs;
   deriving a three-dimensional (3-D) volume of said lesion from said contours;
   determining distances from a reference point to the start and end of said lesion;
   determining the distance from said reference point to a virtual endoscope in said lumen;
   obtaining data on maximum bend characteristics for a said endoscope in a lumen of a given diameter;
   deriving projection criteria, based on said 3-D volume, the lumen diameter, and said maximum bend characteristics;
   projecting an endoluminal image of said lesion based on said projection criteria, said endoluminal image indicating an optimal biopsy insertion point; and
   deriving corrected values for the foregoing distances allowing for said maximum bend characteristics.

2. A method as recited in claim 1, wherein said step of deriving projection criteria comprises deriving a set of surface normals to said lumen wall and changing the respective angles of said normals based on said 3-D volume, the lumen diameter, and said maximum bend characteristics for obtaining a set of modified normals.

3. A method as recited in claim 1, wherein said step of projecting an endoluminal image of said lesion comprises utilizing said set of modified normals to define said endoluminal image.

4. A method as recited in claim 1, wherein said step of projecting an endoluminal image comprises a step of indicating thereon the respective depths of said lesion corresponding to respective points on said endoluminal image.

5. A method as recited in claim 4, wherein said step of indicating respective depths comprises a step of determining said respective depths along respective ones of said set of modified normals.

6. A method as recited in claim 4, wherein said step of projecting an endoluminal image comprises a step of indicating thereon the respective depths of said lesion corresponding to respective points on said endoluminal image.

7. A method as recited in claim 4, wherein said step of indicating the respective depths of said lesion comprises one of
(a) shading said image to indicate depth and
(b) color coding said image to indicate depth.

8. A method as recited in claim 7, including a step outputting information on the rotational angle of said virtual endoscope.

9. A method as recited in claim 7, including a step performing a real endoscopy utilizing information from said virtual endoscopy, including identifying said reference point, utilizing said corrected values, and said respective depths for inserting a biopsy needle at said optimal biopsy insertion point.

10. A method as recited in claim 7, including a step aligning said biopsy needle along a respective modified normal at said optimal biopsy insertion point.

11. A method as recited in claim 8, including a step performing a real endoscopy utilizing information from said virtual endoscopy, including identifying said reference point, utilizing said corrected values, said information on the rotational angle, and said respective depths for inserting a biopsy needle at said optimal biopsy insertion point.

12. A method as recited in claim 1, wherein said step of acquiring from a patient an imaging dataset comprises acquiring a data set of the bronchial airway.

13. A method for virtual endoscopy in a lumen, comprising:
acquiring from a patient an imaging dataset exhibiting a lesion external to a lumen wall;
drawing planar contours around said lesion;
deriving a three-dimensional (3-D) volume of said lesion;
obtaining data on maximum bend characteristics for a given endoscope; and
deriving projection criteria, based on said 3-D volume and said maximum bend, for projecting an endoluminal image of said lesion indicating an optimal biopsy insertion point.

14. A method as recited in claim 13, wherein said step of deriving projection criteria comprises deriving a set of normals to said lumen wall and changing the respective angles of said normals based on said 3-D volume, the lumen diameter, and said maximum bend characteristics for obtaining a set of modified normals.

15. A method as recited in claim 14, wherein said step of projecting an endoluminal image of said lesion comprises utilizing said set of modified normals to define said endoluminal image.

16. A method as recited in claim 13, wherein said step of projecting an endoluminal image comprises a step of indicating thereon the respective depths of said lesion corresponding to respective points on said endoluminal image.

17. A method as recited in claim 15, wherein said step of indicating respective depths comprises a step of determining said respective depths along respective ones of said set of modified normals.

18. A method as recited in claim 15, wherein said step of projecting an endoluminal image comprises a step of indicating thereon the respective depths of said lesion corresponding to respective points on said endoluminal image.

19. A method as recited in claim 15, wherein said step of indicating the respective depths of said lesion comprises one of
(a) shading said image to indicate depth and
(b) color coding said image to indicate depth.

20. A method as recited in claim 19, including a step outputting information on the rotational angle of said virtual endoscope.

21. A method as recited in claim 19, including
determining distances from a reference point to the start and end of said lesion; and
determining the distance from said reference point to a virtual endoscope in said lumen.

22. A method as recited in claim 21, including a step of performing a real endoscopy utilizing information from said virtual endoscopy, including identifying said reference point, utilizing said corrected values, and said respective depths for inserting a biopsy needle at said optimal biopsy insertion point.

23. A method as recited in claim 22, including a step aligning said biopsy needle along a respective modified normal at said optimal biopsy insertion point.

24. A method as recited in claim 21, including a step of utilizing an endoscope having the characteristics of said virtual endoscope.

25. A method as recited in claim 22, including a step of performing a real endoscopy utilizing information from said virtual endoscopy, including identifying said reference point, utilizing said corrected values, said information on the rotational angle, and said respective depths for inserting a biopsy needle at said optimal biopsy insertion point.

26. A method as recited in claim 13 wherein said step of acquiring from a patient an imaging dataset comprises acquiring a data set of the bronchial airway.

27. A system for virtual endoscopy in a lumen, comprising:
means for acquiring from a patient an imaging dataset exhibiting a lesion external to a lumen wall;
generating multiplanar reformations (MPRs) from said dataset;
drawing planar contours around said lesion;
means for deriving a three-dimensional (3-D) volume of said lesion;
means for obtaining data on maximum bend characteristics for a given endoscope; and
means for deriving projection criteria, based on said 3-D volume and said maximum bend, for projecting an endoluminal image of said lesion, indicating an optimal biopsy insertion point.

28. A method for virtual endoscopy in a lumen, comprising:
acquiring a dataset from a patient using an imaging technique such as CT or MRI;
generating multiplanar reformations (MPRs) from said dataset, comprising two-dimensional (2D) sections;
displaying a virtual endoscopic view utilizing said dataset;
drawing planar contours around lesions in said MPRs;
calculating a 3-D volume from the planar contours;

displaying the 3-D volume in an endoluminal view;
selecting a reference point;
utilizing software to display the distances between said reference point to the start and endpoints of a lesion and to a virtual endoscope position;
utilizing software to display the maximal bending angle of an endoscope in a selected insertion area, a corrected distance to said reference point after bending, and to project an insertion point onto the endoluminal wall in said selected insertion area, and optionally, to display rotational information; and
guiding a real endoscope in a patient to said insertion point using information from said virtual bronchoscopy.

29. A computer program product comprising a computer useable medium having computer program logic recorded thereon for program code for performing a method for virtual endoscopy in a lumen, comprising:
acquiring from a patient an imaging dataset exhibiting a lesion external to a lumen wall;
deriving a three-dimensional (3-D) volume of said lesion;
obtaining data on maximum bend characteristics for a given endoscope; and
deriving projection criteria, based on said 3-D volume and said maximum bend, for projecting an endoluminal image of said lesion, indicating an optimal biopsy insertion point.

30. A method for virtual endoscopy within a cavity, comprising:
acquiring from said cavity an imaging dataset including a feature of interest external to a cavity wall;
drawing contours around said feature;
deriving a three-dimensional (3-D) volume of said feature from said contours;
determining distances from a reference point to the start and end of said feature;
determining the distance from said reference point to a virtual endoscope in said cavity;
obtaining data on maximum bend characteristics for said endoscope corresponding to said cavity dimensions;
deriving projection criteria, based on said 3-D volume, said cavity dimensions, and said maximum bend characteristics;
projecting an endoluminal image of said feature based on said projection criteria, said endoluminal image indicating an optimal access point; and
deriving corrected values for the foregoing distances allowing for said maximum bend characteristics.

31. A method as recited in claim 30, wherein said step of deriving projection criteria comprises deriving a set of surface normals to said cavity wall and changing the respective angles of said normals based on said 3-D volume, said cavity dimensions, and said maximum bend characteristics for obtaining a set of modified normals.

32. A method as recited in claim 31, wherein said step of projecting an endoluminal image of said feature comprises utilizing said set of modified normals to define said endoluminal image.

33. A method as recited in claim 30, wherein said step of projecting an endoluminal image comprises a step of indicating thereon the respective depths of said feature corresponding to respective points on said endoluminal image.

34. A method as recited in claim 33, wherein said step of indicating respective depths comprises a step of determining said respective depths along respective ones of said set of modified normals.

35. A method as recited in claim 33, wherein said step of projecting an endoluminal image comprises a step of indicating thereon the respective depths of said feature corresponding to respective points on said endoluminal image.

36. A method as recited in claim 33, wherein said step of indicating the respective depths of said feature comprises one of
(a) shading said image to indicate depth and
(b) color coding said image to indicate depth.

37. A method as recited in claim 36, including a step outputting information on the rotational angle of said virtual endoscope.

38. A method as recited in claim 36, including a step performing a real endoscopy utilizing information from said virtual endoscopy, including identifying said reference point, utilizing said corrected values, and said respective depths for inserting a tool at said optimal insertion point.

39. A method as recited in claim 38 including a step aligning said tool along a respective modified normal at said optimal insertion point.

40. A method as recited in claim 37, including a step performing a real endoscopy utilizing information from said virtual endoscopy, including identifying said reference point, utilizing said corrected values, said information on the rotational angle, and said respective depths for inserting a tool at said optimal insertion point.

41. A method for virtual endoscopy in a cavity, comprising:
acquiring an imaging dataset exhibiting a feature of interest external to a wall of said cavity;
deriving a three-dimensional (3-D) volume of said feature of interest;
obtaining data on maximum bend characteristics for a given endoscope; and
deriving projection criteria, based on said 3-D volume and said maximum bend, for projecting an endoluminal image of said feature of interest.

42. A method as recited in claim 41, wherein said step of deriving projection criteria comprises deriving a set of normals to said lumen wall and changing the respective angles of said normals based on said 3-D volume, the cavity diameter, and said maximum bend characteristics for obtaining a set of modified normals.

43. A method as recited in claim 41, wherein said step of projecting an endoluminal image of said feature of interest comprises utilizing said set of modified normals to define said endoluminal image.

44. A method as recited in claim 41, wherein said step of projecting an endoluminal image comprises a step of indicating thereon the respective depths of said feature of interest corresponding to respective points on said endoluminal image.

45. A method as recited in claim 44, wherein said step of indicating respective depths comprises a step of determining said respective depths along respective ones of said set of modified normals.

46. A method as recited in claim 44, wherein said step of projecting an endoluminal image comprises a step of indicating thereon the respective depths of said feature of interest corresponding to respective points on said endoluminal image.

47. A method as recited in claim 44, wherein said step of indicating the respective depths of said feature of interest comprises one of
(a) shading said image to indicate depth;
(b) color coding said image to indicate depth; and
(c) shading and color coding said image to indicate depth.

48. A method as recited in claim 47, including a step outputting information on the rotational angle of said virtual endoscope.

49. A method as recited in claim 47, including
   determining distances from a reference point to the start and end of said feature of interest; and
   determining the distance from said reference point to a virtual endoscope in said lumen.

50. A method as recited in claim 49, including a step of performing a real endoscopy utilizing information from said virtual endoscopy, including identifying said reference point, utilizing said corrected values, and said respective depths for inserting a tool.

51. A method as recited in claim 50, including a step of aligning said tool along a respective modified normal at said optimal insertion point.

52. A method as recited in claim 49, including a step of utilizing an endoscope having the characteristics of said virtual endoscope.

53. A method as recited in claim 49, including a step of performing a real endoscopy utilizing information from said virtual endoscopy, including identifying said reference point, utilizing said corrected values, said information on the rotational angle, and said respective depths for inserting a tool at said optimal tool insertion point.

54. A method as recited in claim 41, wherein said step of acquiring an imaging dataset comprises acquiring a data set of said cavity.

55. A method for virtual endoscopy in a lumen, comprising:
   deriving a three-dimensional (3-D) volume of a lesion;
   obtaining data on maximum bend characteristics for a given endoscope; and
   deriving projection criteria, based on said 3-D volume and said maximum bend, for projecting an endoluminal image of said lesion indicating an optimal biopsy insertion point.

\* \* \* \* \*